United States Patent [19]

Hunt et al.

[11] Patent Number: 4,922,337

[45] Date of Patent: May 1, 1990

[54] TIME DELAY AND INTEGRATION OF IMAGES USING A FRAME TRANSFER CCD SENSOR

[75] Inventors: Robert P. Hunt, Palo Alto; David L. Gilblom, Los Altos, both of Calif.

[73] Assignee: Picker International, Inc., Highland Hts, Ohio

[21] Appl. No.: 249,385

[22] Filed: Sep. 26, 1988

Related U.S. Application Data

[63] Continuation-in-part of Ser. No. 186,446, Apr. 26, 1988.

[51] Int. Cl.[5] .............................................. H04N 7/18
[52] U.S. Cl. ................................... 358/101; 358/106; 358/213.26; 250/572
[58] Field of Search ................. 358/101, 106, 107, 93, 358/909, 213.13, 213.23, 213.25, 213.26, 213.31, 213.29; 382/8; 356/237; 250/223 R, 562, 563, 572, 578; 378/17, 98, 99

[56] References Cited

U.S. PATENT DOCUMENTS

| | | | |
|---|---|---|---|
| Re. 32,164 | 5/1986 | Kruger | 378/19 |
| 4,366,574 | 12/1982 | Hill | 378/99 |
| 4,546,444 | 10/1985 | Ballis | 250/572 X |
| 4,578,810 | 3/1986 | MacFarlane et al. | 382/8 |
| 4,663,669 | 5/1987 | Kinoshita et al. | 358/213.19 |
| 4,668,982 | 5/1987 | Tinnerino | 358/106 X |
| 4,668,983 | 5/1987 | Werson | 358/101 X |
| 4,689,686 | 8/1987 | Hashimoto et al. | 358/213.19 X |
| 4,811,409 | 3/1989 | Cavan | 382/8 |

Primary Examiner—James J. Groody
Assistant Examiner—Victor R. Kostak
Attorney, Agent, or Firm—Fay, Sharpe, Beall, Fagan, Minnich & McKee

[57] ABSTRACT

A tachometer (32) monitors the speed of a continuously moving web or article (12). A lens (20) focuses an image of a portion of the web in an examination region (14) on image section (22) of a CCD array. As the web moves, the image moves correspondingly along the image section. A synchronizing circuit (C) adjusts the frequency of the tachometer output signal and uses it in lieu of a fixed frequency oscillator as the master clocking or timing basis for generating clocking pulses for the CCD array. More specifically, the synchronizing circuit generates four phase clocking pulses ($\phi 1A-\phi 4A$) which shifts lines of CCD data along the image section at the same speed that the image is moving along the CCD section. In this manner, the pixel values integrate light from the same area of the imaged web at each shifted position along the image section. Each line of data from the image section may be shifted at the same rate through an optically light-insensitive storage section (24) and read out serially by shift registers (26) to form a video signal. A quality control analysis circuit (D) monitors the video signal for selected characteristics of the imaged web. Preferably, a record is maintained of the location of flaws and defects noted by the quality analysis circuit.

19 Claims, 4 Drawing Sheets

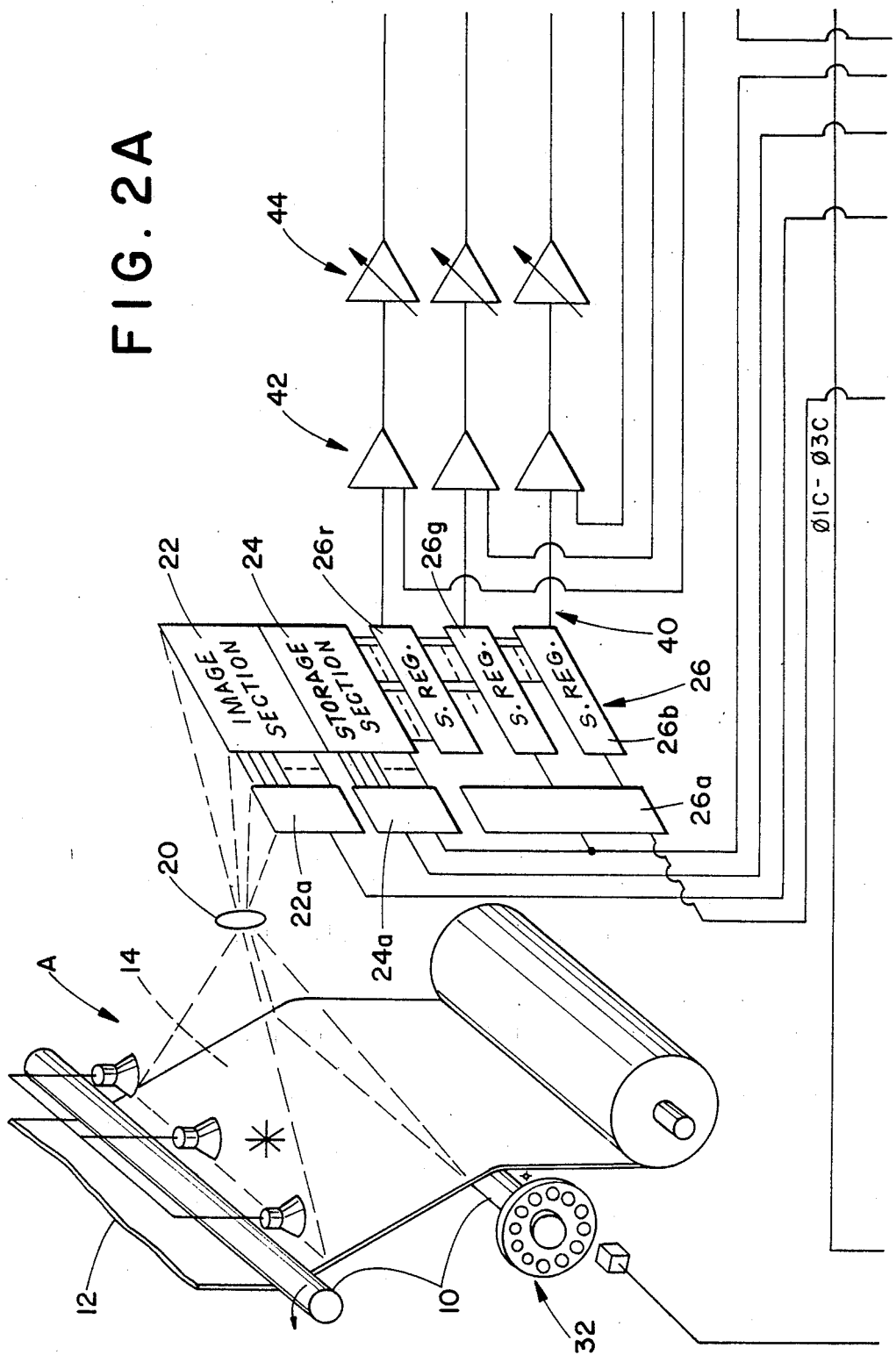

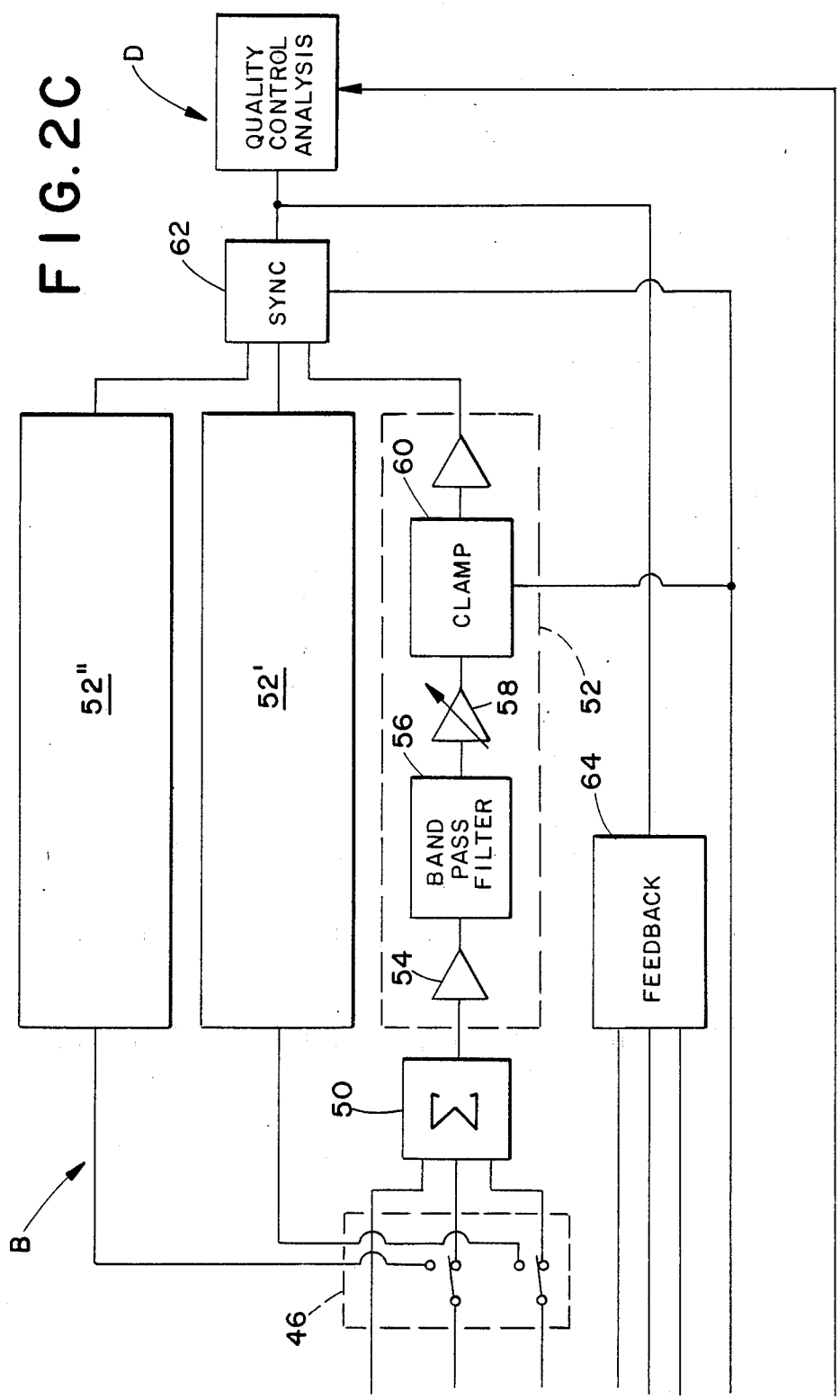

TIME DELAY AND INTEGRATION OF IMAGES USING A FRAME TRANSFER CCD SENSOR

This application is a continuation-in-part of U.S. patent application Ser. No. 186,446, filed Apr. 26, 1988.

BACKGROUND OF THE INVENTION

The present invention relates to the video camera art. It finds particular application in conjunction with quality control and monitoring with video cameras, especially of continuous material processes, and will be described with particular reference thereto. It is to be appreciated that the invention may find other applications including document reading, photographic archival recording, object tracking, video security, and the like.

Heretofore, quality control and monitoring has been carried out with charge coupled devices (CCD) and other video cameras. In one method, a video output signal was generated which included a long, continuous series of video image fields. In a frame transfer CCD camera, light from a continuous or pulsed source was focused on an image section of a CCD sensor for a selected interval of time. The interval was selected to produce good image contrast without significant blurring of the image due to object motion. The charge on each element of the image section was indicative of received light intensity. The charge was transferred during a vertical blanking interval, e.g. a few hundred microseconds, into corresponding elements of an optically insensitive CCD mass storage section. As the image section again commenced integrating received light, the charge was read out element by element from the optically insensitive elements to form a video signal representing one field of the resultant image. After the 1/60th of a second or other selected read out interval, the charge representing the second field was transferred from the image section to the storage section. As the second field was read out of the storage section, the second video signal image section started integrating light to form a third field. This sequence was repeated cyclically to form a video signal representing a series of single image fields.

Continuous production of image fields rendered CCD cameras awkward to adapt for certain high volume quality control situations. As a continuous sheet or individual object was moved past the CCD camera, the resultant video signal represented a long series of image fields. In order to review the images of each object to monitor for a controlled characteristic, it was first necessary to determine which portion of the video signal included the field(s) which represented the monitored individual object or portion of the continuous sheet. Second, it was necessary to determine within the field the actual location of the monitored object or sheet portion. When increased lighting was necessary, the actuation of a strobe light was coordinated with the field of interest. If the strobe light was not completely coincident with a common location of the object or sheet portion within the field(s) of interest, lighting intensities and object shapes would vary among the fields of interest for each object or sheet portion. If the stream of objects or sheet was moving rapidly compared with 1/60th of a second or other one field exposure time, then each object would be in a different position within the selected field of interest. This different positioning of the object not only required identifying the object position in the video field, but could also result in different lighting conditions on the object. These inaccuracies in the timing, positioning, and lighting of the monitored objects all limited the degree of accuracy and the speed with which quality control monitoring could be performed.

In the quality control and monitoring method described in parent patent application Ser. No. 186,446, filed Apr. 28, 1988, a CCD device is asynchronously triggered at a controlled instant in time to "grab" a moving object. The instant in time is synchronized with the moving object's entry to a preselected examination point. A high intensity strobe is flashed concurrently with asynchronously triggering a CCD device to "grab" the moving object. While such a method has certain unique advantages, it requires a significant amount of power capacity to flash the high intensity light necessary for its functioning. The minimum cycle time of the strobe limited the speed of the conveying system.

Although asynchronous triggering is applicable to continuous web monitoring, some webs are advanced at such high speeds that the repower time of the strobe may limit the web advancement speed. Additionally, inspection of continuous webs with cameras producing a series of individual fields that requires matching the tops and bottoms of adjacent fields to provide a single, complete image of the web without gaps or overlaps. Processes in which continuous webs are advanced include the fabrication of sheets and films of plastics such as polyethylene, MYLAR, cellophane and vinyl, metals, glass, plywood, paper and other wood pulp products, fabrics, printing of newspapers, magazines, wallpaper, packaging, etc., lamination of plastics, composites, paper, etc., coating of plastics, metals, etc. with paint, magnetic particles, abrasives, adhesives, photographic emulsions, electrically conductive materials, etc., and embossing, cutting, slitting, perforating, etc. of any of the aforementioned raw or processed materials.

Previous inspection of continuous web materials was carried out using either CCD cameras in the raster-scan mode with stroboscopic illumination or by using line-scan cameras with intense continuous illumination. Line scan cameras were constructed with a single row of photosensitive areas or sensors. A large amount of illumination was necessary to produce usable signals from the sensor. Because the sampling of the single line of sensors was controlled by an external clock, there were gaps or overlap in the monitored web, depending on the speed of the web.

Both the raster-scan and the line scan cameras created distortions in the image data. In the case of the raster-cameras, the top and bottom edges of the images had to be found and the overlap or missed material corrected. In the case of line-scan cameras, the increment of material covered by each scan could be different if web speed changed.

Even if the line-scan and raster-scan cameras were synchronized with the moving web, problems still remained. In the case of the raster-camera, the top and bottom edges still had to be matched and high power, stroboscopic illumination was required. In the case of line-scan cameras, the time that the line of photodiodes was exposed to light was very short. Accordingly, very brilliant illumination was required. The light requirements, whether stroboscopic or high intensity, became so burdensome that the maximum speed of the web material was limited.

The present invention contemplates a new and improved video camera system and method which overcomes the above referenced problems and others.

SUMMARY OF THE INVENTION

In accordance with one aspect of the present invention, a synchronously controlled CCD camera is provided. A lens focuses light from an examination region onto the elements of an image section of a CCD light sensor array. A control means sends clock pulses to an image section and a storage section of the CCD camera. The clock pulses cause pixel charges indicative of cumulative light received by light sensors in the image section to move down the image section into the storage section synchronously with movement of the monitored subject. Additional clock pulses control transferring pixel charges out from each element of the storage section to produce a serial video signal.

In accordance with a more limited aspect of the invention, a synchronization means synchronizes the clocking of the pixel charges down the image and storage sections of the CCD array with the movement of a monitored web or objects. The synchronization is such that the imaged area of the product impressed upon the light sensor area is superimposed upon the light values representing the same area of image previously monitored throughout the integration period. That is, as movement of the object causes the image of a preselected object portion to move along the CCD array, the clock pulses shift the corresponding electronic light value or charge the equivalent distance and direction along the CCD array.

A first advantage of the present invention is that it consumes less electrical power than systems using high intensity flashes to illuminate the object.

Another advantage of the present invention is that it permits monitoring under lower levels of lighting and non-flashed lighting.

Another advantage of the present invention is that it allows for monitoring of a continuous web process without overlapping. Identifying and recognizing the overlap between frames is eliminated.

Yet another advantage of the present invention is that it refreshes pixel light values representing light received by light sensors, throughout the integration period.

Still further advantages of the present invention will become apparent to those of ordinary skill in the art upon reading and understanding of the following detailed description.

BRIEF DESCRIPTION OF THE DRAWINGS

The present invention may take form in various components and arrangements of components or in various steps and arrangements of steps. The figures are only for purposes of illustrating a preferred embodiment and are not to be construed as limiting the invention.

DETAILED DESCRIPTION OF THE PREFERRED EMBODIMENT

Figure 1:
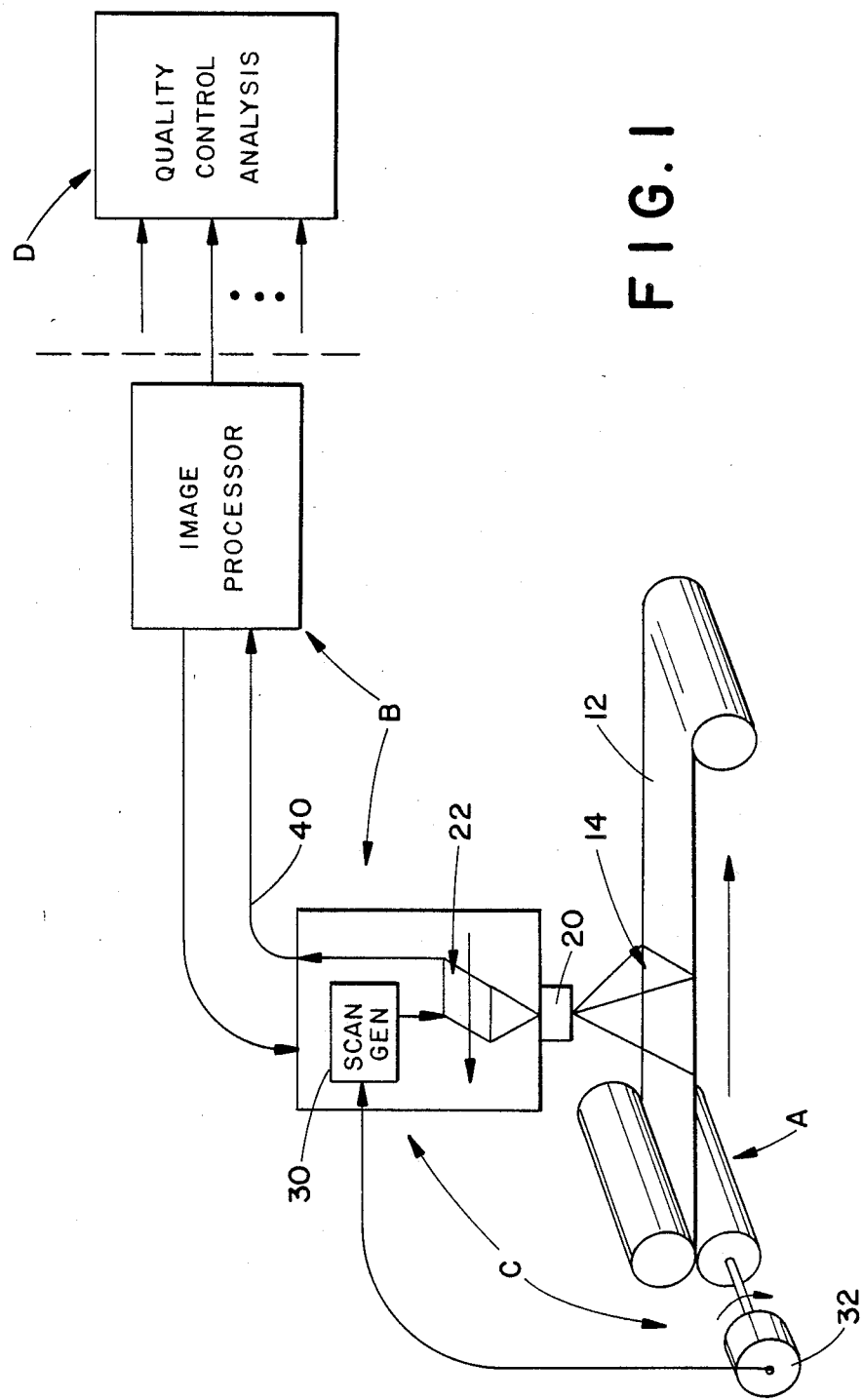
FIG. 1 is a diagrammatic illustration of a quality control system in accordance with the present invention; and, FIGS. 2A, 2B and 2C taken together are a more detailed illustration of the system of FIG. 1.

With reference to FIG. 1, conveying means A moves a continuous web or other object(s) to be examined through an examination region at an adjustable speed. A CCD camera or opto-electrical transducer system B monitors the moving object by focusing an image of the moving object on an opto-electric transducer. As the object moves, the image moves correspondingly along the transducer. A synchronizing control means C synchronizes and coordinates movement of the object and conversion of the image into an electronic video signal by the camera. Specifically, the transducer samples the same element or pixel of an image several times. The synchronizing means causes the multiple samplings corresponding to the same pixel of the image but sampled at different regions of the transducer to be integrated. The synchronizing means preferably adapts the sampling of the transducer to movement of the object. However, in some applications it is advantageous to vary the speed of the object to match the sampling of the transducer. A quality control analysis means D analyses the video signal for flows, defects, or other characteristics of the web and denotes their locations.

With continuing reference to FIG. 1 and further reference to FIG. 2A, the conveying means A includes a conventional conveyor 10 for moving object 12 through the examination region 14. The nature of the conveyor is dependent on the object to be transported, as is known in the art. In the preferred embodiments, the conveyor includes rollers for a continuous web of floor coverings, wall paper, or other finished sheet goods. The continuous web may include polymeric films such as MYLAR, CELANAR, KAPTON, vinyls, plywood, paper products, etc. Alternatively, the conveyer may include a belt for carrying the articles. Optionally, the conveyor may have pockets, recesses, or clamps for fixing the position of each received object on the belt.

The camera B includes an optical system, such as a lens 20, which focuses light received from the examination region on a light sensitive area 22, preferably a bidirectional array of CCD elements. The lens focuses light emanating from the examination region continuously onto the light sensitive area or image section of the optoelectrical transducer. The resolution of the resultant image is determined by the number of CCD elements in each dimension. The more elements, the finer the resolution. A typical video camera might have a 244×610 element array. For color, a third of the elements have a green filter, a third have a blue filter, and a third have a red filter, or any other three color filter combination as is conventional in the art.

In conventional frame transfer CCD cameras, the data is periodically shifted from the image section 22 to a light shielded storage section 24 during a vertical flyback period which erases or resets each element of the CCD image section. In the TDI mode, the vertical flyback signals are defeated. The image section and storage section transfer are both connected the synchronizing means C to which step lines of pixels continuously at a line frequency rate to output registers 26. The synchronizing means controls the lines or rows of the photosensors 22, 24 in such a way that the accumulated charge is moved in synchronization with the light pattern impinging upon the photosensors from the moving web. That is, as the web moves some small increment, the charge is shifted one row to follow the motion. If there are, for example, 256 rows of photoelements, then the total exposure time for each small area of the image will be 256 times as long as a single row imager or line scan camera. Because each incremental element of the moving web is imaged 256 times, once in each row, the web may move 256 times faster or the intensity of illumination may be reduced by 256. This technique, of course, can also be applied to interline-transfer CCD imagers with the use of more complex support circuitry. For example, when the web has a spot or blemish which passes through the examination region, the image of the spot is progressively transferred or shifted along the light sensitive area into the storage section 24.

That is, the charge values are shifted from row to row along the CCD array in precise synchronization with movement of the object being imaged and its image on the CCD array. For example, if the lens 20 focuses a 1 millimeter×1 millimeter area of the object on each element of the CCD array, then each time the object moves 1 millimeter, the pixel or integrated light values are shifted one row or line in the CCD array. In this manner, subsequent images on the CCD array superimpose directly on shifted previous images. By the time an image value or line of image values reaches the optically insensitive storage section 24 of the sensor, the optic information from the object has been integrated over the entire transfer period (1/10 seconds, for example). With the 244×610 CCD array, each pixel value represents the sum of light received at each of 244 CCD elements. The synchronization means C keeps monitored object movement and the image sensor transfer process in precise synchronization. In the preferred embodiment, the speed of the conveyor rollers, drive motors, or the like is converted by the synchronization means into clocking signals for the CCD array. Alternatively, signals from clocking electronics in the camera may readjust and control the speed of the drive motors of the conveyor.

Figure 2B:
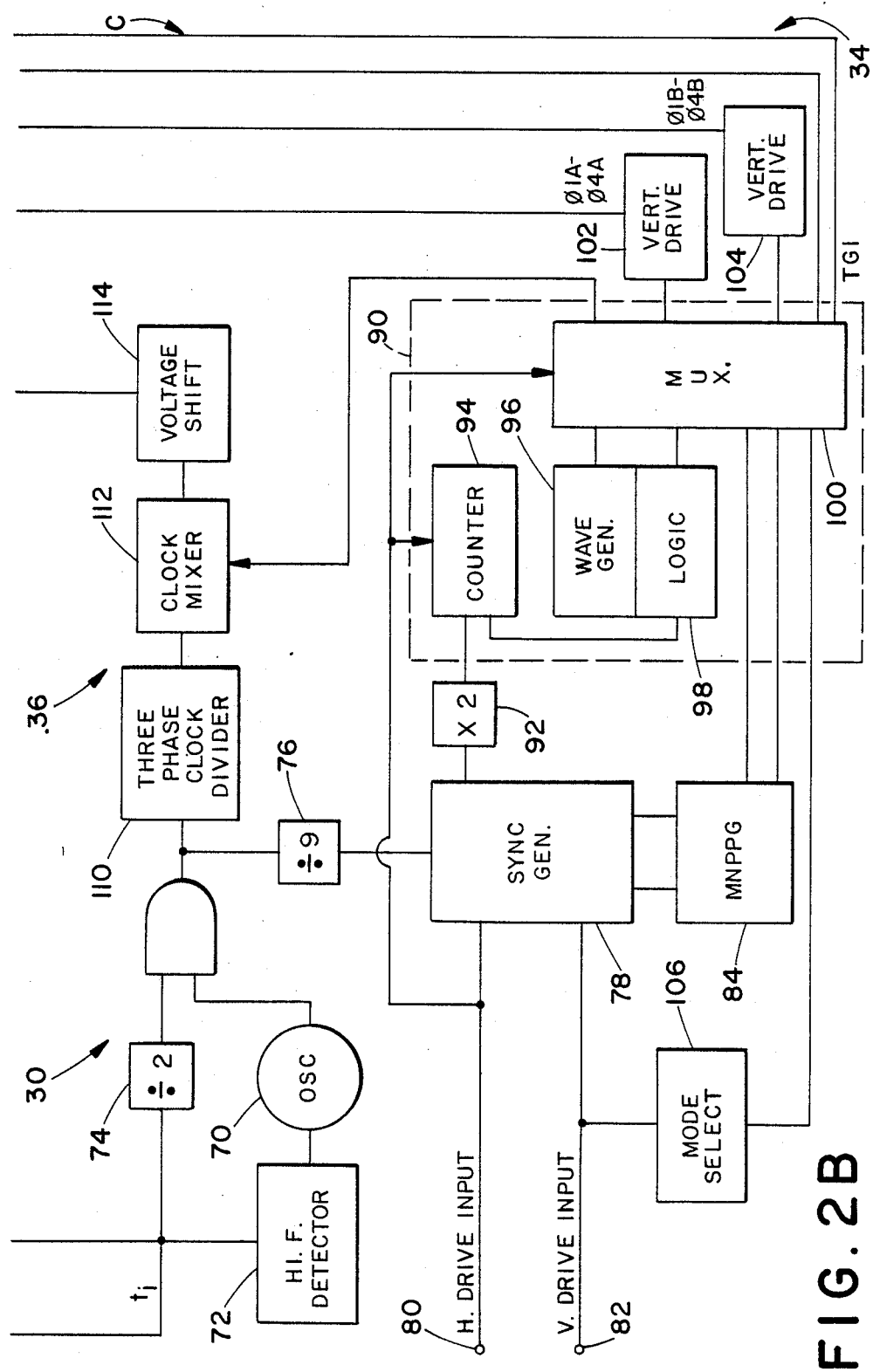

With combined reference to FIGS. 2A and 2B, clocking electronics 30 receives a trigger signal $t_i$ from a conveyor speed sensor or tachometer 32 and produces clock pulses $\phi 1A-\phi 4A$ and $\phi 1B-\phi 4B$ to clock the CCD array at a corresponding rate. More specifically, the trigger signals control the frequency of an image section transfer clock or means 34, which supplies the clock signals to a light image sensor section control means 22a and a storage section control means 24a. The light image sensor control means 22a causes the charge of each image element or row of elements of the image section 22 to be shifted. More specifically, the four phase image section transfer clock signal $\phi 1A-\phi 4A$ shifts the charge line by line. After just about 244 pulses or shift commands in the illustrated 244 active line image section embodiment, a line of charge values has been shifted 244 lines from the first line of the image section into the storage section 24.

The clocking signals are selected such that the image transfer is synchronized with the movement of the conveyor. The controller C conveys identical transfer clock pulses $\phi 1B-\phi 4B$ to the storage section control means 24a as sent to the image section control means 22a to cause the data from the storage section 24 to be shifted line by line into the shift registers means 26. To enable the camera to operate in either a conventional field mode or the time delayed integration mode, the storage section is the same size as the image section. If the camera is limited to the time delayed integration mode, the storage section may be much smaller or even eliminated.

For a color video image rendition, a red shift register 26r, a blue shift register 26b, and a green shift register 26g are provided. Once a line of pixel or integrated light values have been transferred from the storage section 24 to the shift registers, a shift register clocking means 36 sends higher speed three phase shift register clock signals $\phi 1C-\phi 3C$ to a shift register controller 26a. The shift registers serially step each charge or data value onto video signal output lines 40 before the next line is loaded into the shift registers from the storage section. Thus, between image or storage section transfer clock pulses, a number of shift register clock pulses equal to the number of elements per line are generated to clock out red, green, and blue output signals.

With continuing reference to FIG. 2A and further reference to FIG. 2C, feedback amplifiers 42 combine each of the three color output signals with a feedback signal which establishes a DC reference level to minimize the interfering effects of clock noise. A gain adjusting amplifier means 44 adjusts the gain of all three signal components correspondingly. A black and white/color mode selecting means 46 selects whether a black and white or color composite video signal is to be produced in accordance with whether a color or black and white image section 22 is provided in the camera.

If a black and white image is selected, a summing means 50 sums the three color components corresponding to each pixel and feeds the data to a first video signal processing channel 52. The video channel includes an impedance adjusting amplifier 54 for providing a low impedance output signal. A band pass filter 56 removes any vestiges of clocking signal noise or the like. A user controlled gain amplifier 58 amplifies the signal from the band pass filter and passes it to a clamping means 60 which restores the DC video. At the end of each horizontal sweep line, the clamping means shorts to a DC reference level to restore a DC level that sets the black level of the resultant image. A synchronization information means 62 switches between lines to reference voltages to add blanking and horizontal synchronization information to the signal. A feedback circuit 64 feeds back a portion of the composite video signal to provide a phase sensitive detection of the clocking to establish the DC level that minimizes the clock noise.

If a color output is selected, then the switching means 46 connects two components of the output signal to analogous video processing channels 52', 52''. By convention, the synchronization means 62 only adds synchronization information to one, generally the green, video component. Preferably, the feedback signal also is based on a single one of the components. The video processing circuitry is stable to better than one part in 256 to enable precision digitizing and digital signal processing of the resultant video signal.

The quality control analysis means D receives the composite video signal and operates on it in a manner that is appropriate to the quality control function undertaken. For example, the analysis means D may turn the composite signal into a man-readable video image. Alternately, the analysis means may examine components of the video signal corresponding to selected regions to determine whether they meet preselected characteristics relative to each other, preselected standards, or the like.

Looking by way of example to monitoring a continuous web of solid color material, the image of the web may change in gray scale or color relative to the rest of the web image. The change may be the result of color changes in the web or surface deformates that alter the amount of reflected light. The pixel values of the video signal of the web are compared with a preselected gray scale characteristic or value to determine if the web is deformed or damaged beyond selected tolerances. If the web has a repeating pattern, the image or video signal is compared with corresponding standards which change cyclically with the pattern to determine whether the web has been accurately processed. If the web is monitored in color, each image or pixel value of the video signal is compared with one of a plurality of colorimetric standards in accordance with a location within the pattern. Alternately, color or other physical parameters may be used to sort various types or grades of products. Numerous other sorting, quality control, and acceptance algorithms may be implemented as are appropriate to the requirements of the objects being examined.

The synchronizing means C further includes a 22.657 MHz internal crystal oscillator 70 for defining the image section transfer clock pulses in a normal interleaved frame video mode. In the time delayed integration mode of the present invention, the trigger signals $t_i$ from the tachometer 32 replace the crystal accelerator as the timing basis. The tachometer in the illustrated embodiment includes a light which shines through apertures of a disc attached to a guide roller that rotates with the conveying means and impinges on a photocell. The photocell sends a trigger pulse $t_i$ each time an incremental length of the continuous web product has passed through the examination region. In this manner, the trigger signal $t_i$ has a frequency that is proportional to the web speed. The frequency of the trigger signal is adjusted by the synchronization means to provide the timing of the transfer clock signals $\phi 1A-\phi 4A$, $\phi 1B-\phi 4B$, sent to the image section control means 22a, and storage section control means 24a. The frequency of the clock signals $\phi 1C-\phi 3C$ send to the read out control means 26a remains substantially constant such that the output signals are at a frequency and format that is compatible with EIA-170 television signal standards regardless of the speed of the web. With particular reference to FIG. 2B, high frequency detector 72 disables crystal oscillator 70 to synchronize the CCD camera with an external master clock signal, e.g. the trigger signal or other signal indicative of web movement. The trigger signal is frequency adjusted to dividers 74, 76 to adjust a sync or master clock frequency generator 78. Initialization pulses are received by a horizontal drive input 80 and vertical drive input 82. The sync generator 78 synchronizes the horizontal and vertical drive pulses with the master clock signal.

A multi norm pulse pattern generator (MNPPG) 84 is controlled by the sync generator and the vertical and horizontal drive signals to provide clock signals for the image section, storage section, and shift register of a conventional CCD video camera operation in a field or frame mode. Commonly, a first four phase clock signal is provided for the image section; a second four phase clock signal is provided for the storage section; and a three phase clock signal is provided for the shift registers. The multi-norm pulse pattern generator also provides transfer gate pulses TG1, optical blanking and clamping pulses, and start and stop pulses to reset the three phase clock.

However, as indicated above, in the time delayed integration mode, the pixel values in only the first line of the CCD array are refreshed each time. These pixel values are shifted along both the image and storage sections at a selectable speed and received light at each position is integrated. This is as opposed to the rapid transfer of pixel values from the image region to the storage region once per field in conventional operation.

A processor 90 replaces the multi norm pulse pattern generator in the time delayed integration mode of the preferred embodiment. A frequency adjusting means 92, e.g. a frequency doubler, adjusts the master clock frequency as is appropriate to the number of lines of elements in the CCD array, the size of the examination region, and the magnification reduction of the camera optic system. A counter 94 counts the clock pulses whose frequency is determined by the tachometer 32. With the illustrated 244 line CCD image section, a divided by 6 counter is utilized such that each increment of the count (up to 244) causes the clock signal to shift the pixel values one line. A TDI wave generator 96 and a logic circuit 98 are addressed by the six bit signal to create and step the four phase clock signal in accordance with counted value. The timing of the clock signal is such that the pixel values shift or step along the image and storage sections synchronously with the movement of the web. More specifically, the generator and logic circuit create a pair of four phase clock signals analogous to the MNPPG clock signals for shifting lines of data from the storage section into the shift register but without the pause for vertical blanking. In the preferred embodiment, the shifting is also at a slower speed than conventional. The three phase clock signal for the shift register is essentially the same as created by the MNPPG. After the count reaches the number of lines in the image section, the logic circuit 98 rests the counter 94. A multiplexor 100 conveys the continuous four phase clock signals to vertical drivers 102 and 104 for the image and storage sections respectively. The outputs of the vertical drivers 102, 104 are continuous four phase clock signals whose frequency and relative phasing are determined by the tachometer 32.

The preferred embodiment can be operated either in the above described time delay integration mode or as a conventional video camera. When the time delayed integration mode is selected, an approximate input on the vertical driver input 82 causes a mode select means 106 to cause the multiplexor to send the above described TDI clock sequences to the vertical drivers 102, 104. An appropriate input on the horizontal drive input 80 initializes the six bit counter. When the conventional frame mode is selected, conventional horizontal and vertical drive signals are applied at inputs 80, 82 which enables the mode select means to cause the multiplexor to pass the conventional clocking output of the MNPPG 84.

The outside master clock signal is also reduced by a three phase clock divider 110. A clock mix means 112 coordinates the three phase clock signals from the three phase clock divider 110 with the four phase image transfer clock signal. A voltage shift means 114 matches the three phase clock signal voltage with the video output shift register control 26a.

The invention has been described with reference to the preferred embodiment. Obviously, modifications and alterations will occur to others upon reading and understanding the preceding detailed description. For example, as previously stated signals from the clocking controller electronics may be used to control the speed of the conveyor system. It is intended that the invention be construed as including all such alterations and modifications insofar as they come within the scope of the appended claims or the equivalents thereof.

Having thus described the preferred embodiment, the invention is now claimed to be:

1. A method of quality control comprising the steps of:
   (a) moving an object to be examined through an examination region;
   (b) monitoring the movement of the object;
   (c) illuminating the object as the object moves through the examination region;
   (d) shifting lines of data values indicative of portions of the object along a sensor array in coordination with the monitored object movement;
   (e) integrating the data values indicative of the same portion of the object as the lines of data values are shifted along the sensor array;
   (f) reading the integrated data values from the sensor array to produce an image output representing a continuous view of the object; and,
   (g) determining at least one characteristic of the object from the image output.

2. The method as set forth in claim 1 wherein the illuminating step includes illuminating the object with a constant light source.

3. The method as set forth in claim 1 wherein the step of monitoring movement of the object includes generating a control signal and in the step shifting the integrated data values, controlling the shifting with the control signal.

4. The method as set forth in claim 1 further including the step of synchronizing the shifting of the integrated data values with the movement of the object.

5. The method as set forth in claim 4 wherein the step of synchronizing the shifting of the integrated sensed values includes adjusting movement of the object.

6. The method as set forth in claim 4 wherein the monitoring step includes generating a control signal indicative of object movement and the synchronizing step includes controlling the shifting of the integrated data values in accordance with the control signals.

7. A method of quality control comprising the steps of:
   (a) moving an object to be examined through an examination region;
   (b) illuminating the object with light from a continuous light source, as the object moves through the examination region;
   (c) projecting an image of the moving object onto an array of image sensor elements, each element integrates light projected thereon into a corresponding pixel value, the image moving across the image sensor with movement of the object;
   (d) shifting the pixel values along the image sensor elements, each element continuing to integrate light projected thereon into the pixel value shifted therealong;
   (e) synchronizing the movement of the object through the examination region and the shifting of the pixel values along the image sensor elements such that each pixel value represents light projected from a corresponding portion of the object integrated by a plurality of the sensor elements;
   (f) serializing the pixel values to produce a video signal representing a video image; and,
   (g) monitoring the video signal for at least one characteristic of the object.

8. The method as set forth in claim 7 wherein the image sensor includes a CCD array which has a light sensing array and a storage array and wherein the step of reading pixel values includes:
   (a) transferring pixel values from the light sensing array to the storage array; and,
   (b) serially transferring the pixel values from the storage array to the output register.

9. The method as set forth in claim 8 further including adding blanking and synchronization signal components to the video signal.

10. The method as set forth in claim 7 wherein the image sensor includes a CCD array which has a light sensing array and a storage array and the object is a continuous web and wherein the step of shifting the pixel values includes:
   shifting the pixel values along the CCD array in proportion to movement of the continuous web, such that subsequent sensing of the object superimposes pixel values corresponding to a common area of the continuous web.

11. The method as set forth in claim 10 further repeating the superimposing step a plurality of times, until the pixel values are transferred into the storage area.

12. The method as set forth in claim 11 further including shifting the pixel values along the light sensing array, transferring the pixel values from the light sensing array to the storage array and shifting the pixel values along the storage array to the shift register at the same clocking speed.

13. A video system comprising:
   a conveying means for transporting an object to be examined through an examination region;
   an optical system for focusing light from the examination region onto an image section having an array of light sensitive elements which are each sensitive to light received through the optical system to produce individual pixel values that are indicative of an amount of light received;
   a transfer means for shifting the pixel values across the light sensitive elements as the optical system continues to focus light from the examination region onto the image section, the light sensitive elements each modifying the pixel value shifted thereto in accordance with the amount of light received;
   a control means for controlling the transfer means such that the pixel values are shifted in synchronization with movement of the conveying means;
   a means for creating a video signal from the pixel values.

14. The system as set forth in claim 13 further including a storage section connected with the image section for receiving pixel values therefrom and wherein the control means causes the transfer means to transfer pixel values from the image section to the storage section in synchronization with the conveying means movement and to transfer the pixel values serially from the storage section to create the video signal.

15. The system as set forth in claim 14 further including a means for connecting the image and storage sections with a common clocking means such that pixel values in the image and storage sections are shifted at a common rate.

16. The system as set forth in claim 13 wherein the control means includes a clock generator for generating clock pulses for controlling shifting of pixel values across the image section.

17. The system as set forth in claim 16 wherein the control means further includes a monitoring means for monitoring speed of the conveying means, the clock generator being connected with the monitoring means such that a frequency of the clock pulses is controlled in accordance with the monitored conveyor speed.

18. A quality control system comprising:
   a conveying means for conveying a continuous web contiguous to a region of interest;
   a two dimensional CCD array having a plurality of lines of light sensitive elements for accumulating lines of pixel values, each pixel value indicative of an accumulated amount of light received;
   a serializing means for serializing pixel values of each line from the CCD array into a video signal at a rate controlled by a received first clocking signal;
   a line shift means for shifting the lines of pixel values along the CCD array to the serializing means at a rate controlled by a received second clocking signal;
   a clock means for generating the second clock signals to control the rate at which the lines of pixel values are transferred along the CCD array;
   a synchronizing means operatively connected with the conveying means and the clock means for synchronizing the transfer of the lines of pixel values along the CCD array with the movement of the conveying means such that each pixel value receives light from the same region of the continuous web as the lines of pixel values are shifted along the CCD array;
   a monitoring means for monitoring the video signal for at least one preselected characteristic; and,
   a recording means for recording an indication of locations along the continuous web at which the preselected characteristic is monitored.

19. A video monitoring method comprising:
   conveying a subject through an examination region;
   illuminating the subject as it moves through the examination region and focusing light reflected therefrom on an array of CCD elements, each element modifying an accumulated charged value thereon in accordance with an amount of light focused thereon;
   shifting the charge values across the array of CCD elements, each element modifying the charge value thereon in accordance with light focused thereon;
   synchronizing movement of the subject through the examination region and the shifting of the charge values along the array of CCD elements; and,
   creating a video signal from the charge values.

* * * * *

UNITED STATES PATENT AND TRADEMARK OFFICE
CERTIFICATE OF CORRECTION

PATENT NO. : B1 4,922,337
DATED : May 3, 1994
INVENTOR(S) : Hunt et al.

It is certified that error appears in the above-indentified patent and that said Letters Patent is hereby corrected as shown below:

On the title page, the following items should read:

[11]    Patent No.:    4,922,337
    [45]    Issued:    May 1, 1990
    [21]    Appl. No.:    249,385
    [22[    Filed:    Sep. 26, 1988

Signed and Sealed this

Twentieth Day of September, 1994

*Attest:*

BRUCE LEHMAN

*Attesting Officer*    *Commissioner of Patents and Trademarks*

REEXAMINATION CERTIFICATE (2292nd)

United States Patent [19]

Hunt et al.

[11] B1 4,922,337

[45] Certificate Issued May 3, 1994

[54] TIME DELAY AND INTEGRATION OF IMAGES USING A FRAME TRANSFER CCD SENSOR

[75] Inventors: Robert P. Hunt, Palo Alto; David L. Gilblom, Los Altos, both of Calif.

[73] Assignee: Picker International, Inc., Highland Hts., Ohio

Reexamination Request:
No. 90/003,128, Jul. 15, 1993

Reexamination Certificate for:
Patent No.: 4,922,337
Issued: Sep. 26, 1988
Appl. No.: 249,385
Filed: May 1, 1990

Related U.S. Application Data

[63] Continuation-in-part of Ser. No. 186,446, Apr. 26, 1988.

[51] Int. Cl.⁵ .............................................. H04N 7/18
[52] U.S. Cl. ............................................ 348/88; 348/92; 348/295; 348/230; 250/208.1; 250/572

[56] References Cited

U.S. PATENT DOCUMENTS

| | | | |
|---|---|---|---|
| Re. 32,164 | 5/1986 | Kruger | 378/19 |
| 3,536,829 | 10/1970 | Gebel | 178/7.1 |
| 3,833,762 | 9/1974 | Gudmundsen | 178/7.1 |
| 3,835,332 | 9/1974 | Bridges | 250/563 |
| 4,223,346 | 9/1980 | Neiheisel et al. | 358/106 |
| 4,278,999 | 7/1981 | Ganguly et al. | 358/213 |
| 4,366,574 | 12/1982 | Hill | 378/99 |
| 4,375,652 | 3/1983 | White | 358/213 |
| 4,382,267 | 5/1983 | Angle | 358/213 |
| 4,546,444 | 10/1985 | Bullis | 364/550 |
| 4,555,636 | 11/1985 | Fujisawa et al. | 250/578 |
| 4,578,810 | 3/1986 | MacFarlane et al. | 382/8 |
| 4,641,256 | 2/1987 | Marchegiano et al. | 364/525 |
| 4,663,669 | 5/1987 | Kinoshita et al. | 358/213.19 |
| 4,668,982 | 5/1987 | Tinnerino | 358/101 |
| 4,668,983 | 5/1987 | Werson | 358/106 |
| 4,689,686 | 8/1987 | Hashimoto et al. | 358/213.26 |
| 4,705,958 | 11/1987 | Sugita | 250/578 |
| 4,743,971 | 5/1988 | Hugli | 358/213.26 |
| 4,811,409 | 3/1989 | Cavan | 382/8 |
| 4,827,142 | 5/1989 | Hatje | 250/563 |
| 4,920,429 | 4/1990 | Jaffe et al. | 358/471 |
| 4,952,809 | 8/1990 | McEwen | 358/213.24 X |

FOREIGN PATENT DOCUMENTS

| | | |
|---|---|---|
| 194331A1 | 9/1986 | European Pat. Off. . |
| 234492A2 | 2/1987 | European Pat. Off. . |
| 331911A2 | 4/1989 | European Pat. Off. . |

OTHER PUBLICATIONS

"Time Delay and Integration Image Sensors", Barbe, Solid State Imaging, Noordhoff International Publishing, Leyden, The Netherlands, 1975, pp. 659–671.

"Charge-Coupled Device and Charge-Injection Device Imaging", Barbe, Journal of Solid-State Circuits, vol. SC-11, No. 1, Feb., 1976 pp. 109–114.

"Self-Scanning CCD Image Sensors Operating As Optoelectrical Transversal Filters", Kleinmeier, undated.

"TDI Charge-Coupled Devices: Design and Applications", Wong, et al., IBM J. Res. Develop. vol. 36, No. 1, Jan. 1992, pp. 83–106.

"Performance of Charge-Coupled Device (CCD) Imaging Sensors", Monro undated.

"TDI-CCD Devices in Document Scanning", Pennington, SPSE Inx. Conf. Electron. Imaging, Nov. 1980, (full paper not published).

"Signal Processing For Time Delay and Integrating Charge-Coupled Device (TDI-CCD) in the Panoramic Scan Mode", Sadowski, SPIE vol. 282 (1981) pp. 115–128.

"Large Time-Delay-and-Integration (TDI) Arrays and Focal Plane Structures With Intrinsic Silicon Response", Dyck, et al., SPIE vol. 282 (1981).

"Long Range E-O Reconnaissance System and Flight Test Results", Palazzo, SPIE vol. 561, (1985) pp. 13–17.

"A 128×1024 Element TDI Image Sensor with Small, High Performance Pixels", Dyck, et al., SPIE vol. 901 (1988) pp. 3–9.

"CCD Imaging Array Combining Fly-s-Eye Lens with TDI for Increased Light-Gathering Ability", Pennington, et al., IBM Technical Disclosure Bulletin, vol. 21, No. 2, Jul. 1978.

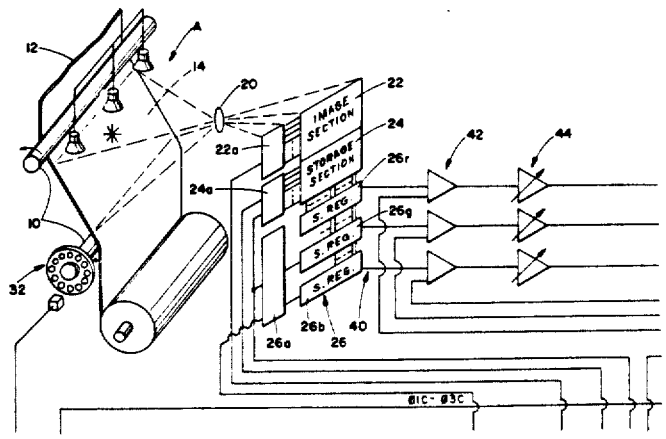

"A TDI Charge-Coupled Imaging Device for Page Scanning", Schlig, IEEE Journ. of Solid-State Circuits, vol. SC-21, No. 1, Feb. 1986 pp. 182–186.

"A Spatial Image Separator for Color Scanning", Gutleben, et al., SPIE vol. 809 (1987), pp. 52–54.

"Document Scanning With a New Family of Experimental High-Performance TDI-CCD Imaging Devices", Yao, et al., Electronic Imaging '88 Int. Electronic Imaging Exposition and Conference, Advance Printing of Paper Summaries, vol. 2, (1988) pp. 566–570.

"Signal-to-Noise Ratio Dependence on Frame Time, Time Delay and Integration (TDI), and Pulse Shaping", Cox, SPIE vol. 244, (1980) pp. 167–181.

"A Buttable 2048×96 Element TDI Imaging Array", Ellul, et al., SPIE vol. 501 (1984), pp. 117–127.

"Charge Imaging Matrix For Infrared Scanning", Borrello, et al., SPIE vol. 409 (1983), pp. 69–75.

"Time-Delay-And-Integration Charge Coupled Devices (CCDs) Applied to the Thematic Mapper", Thompson, et al., SPIE vol. 143 (1978) pp. 19–27.

"The Application of CCD Detectors to UV Imaging From a Spinning Satellite", Murphree, et al., SPIE vol. 932 (1988) pp. 42–49.

"P8602 Charge Coupled Device (CCD) Image Sensor", 1984 English Electric Valve Company Limited, Feb. 1984, pp. 1–4.

"Diverse Electronic Imaging Applications For CCD Line Image Sensors", Hunt, et al.

"A Time Delay and Integration CCD For a Serial Scanned IR Imager", Vanstone, et al., pp. 315–325.

"10,240 Pixel Focal Plane with Five Butted 2,048×96 Element TDI CCDs", Bradley, et al.

"An Ultraviolet Auroral Imager For the Viking Spacecraft", Anger, et al. Geophysical Research Letters, vol. 14, No. 4, pp. 387–390, Apr. 1987.

"Moving Target Sensors", Final Report, Contract No. N00039-73-C-0070, Prepared For: Dept. of the Navy, by Texas Instruments Incorp. 29 Oct. 1973.

"Charge Coupled Device (CCD) Image Sensor"; English Electric Valve Company Limited; pp. 1–4; Feb. 1984.

"A PC-Based Real Time Defect Imaging System For High Speed Web Inspection"; Roberts et al; undated; pp. 7/29–7/41.

*Primary Examiner*—Victor R. Kostak

[57] ABSTRACT

A tachometer (32) monitors the speed of a continuously moving web or article (12). A lens (20) focuses an image of a portion of the web in an examination region (14) on image section (22) of a CCD array. As the web moves, the image moves correspondingly along the image section. A synchronizing circuit (C) adjusts the frequency of the tachometer output signal and uses it in lieu of a fixed frequency oscillator as the master clocking or timing basis for generating clocking pulses for the CCD array. More specifically, the synchronizing circuit generates four phase clocking pulses ($\phi 1A$–$\phi 4A$) which shifts lines of CCD data along the image section at the same speed that the image is moving along the CCD section. In this manner, the pixel values integrate light from the same area of the imaged web at each shifted position along the image section. Each line of data from the image section may be shifted at the same rate through an optically light-insensitive storage section (24) and read out serially by shift registers (26) to form a video signal. A quality control analysis circuit (D) monitors the video signal for selected characteristics of the imaged web. Preferably, a record is maintained of the location of flaws and defects noted by the quality analysis circuit.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7–19 are confirmed.

Claim 1 is determined to be patentable as amended.

Claims 2–6 dependent on an amended claim, are determined to be patentable.

New claims 20–23 are added and determined to be patentable.

1. A method of quality control comprising the steps of:
   a) [moving] *conveying* an object to be examined through an examination region *on a continuous conveying means;*
   b) monitoring the movement of the object;
   c) illuminating the object as the object moves through the examination region;
   d) shifting lines of data values indicative of portions of the object along a sensor array in coordination with the monitored object movement;
   e) integrating the data values indicative of the same portion of the object as the lines of data values are shifted along the sensor array;
   f) reading the integrated data values from the sensor array to produce an image output representing a continuous view of the object; and,
   g) determining at least one characteristic of the object from the image output.

*20. A method of quality control comprising the steps of:*
   *a) moving an object to be examined through an examination region;*
   *b) monitoring the movement of the object for velocity changes;*
   *c) illuminating the object as the object moves through the examination region;*
   *d) changing in real time a rate of shifting lines of data values indicative of portions of the object along a sensor array in coordination with the monitored velocity changes;*
   *e) integrating the data values indicative of the same portion of the object as the lines of data values are shifted along the sensor array;*
   *f) reading the integrated data values from the sensor array to produce an image output representing a continuous view of the object; and,*
   *g) determining at least one characteristic of the object from the image output.*

*21. A method of quality control comprising the steps of:*
   *a) moving a continuous web to be examined through an examination region;*
   *b) monitoring a speed of movement of the continuous web through the examination region;*
   *c) illuminating the continuous web as the continuous web moves through the examination region;*
   *d) shifting lines of data values indicative of portions of the continuous web along a sensor array in coordination with the monitored continuous web speed;*
   *e) integrating the data values indicative of the same portion of the continuous web as the lines of data values are shifted along the sensor array;*
   *f) reading the integrated data values from the sensor array to produce an image output representing a view of the continuous web; and,*
   *g) determining at least one characteristic of the continuous web from the image output.*

*22. A method of quality control comprising the steps of:*
   *a) moving an object to be examined through an examination region;*
   *b) monitoring the movement of the object;*
   *c) illuminating the object as the object moves through the examination region;*
   *d) shifting lines of data values indicative of portions of the object along a sensor array in coordination with the monitored object movement;*
   *e) integrating the data values indicative of the same portion of the object as the lines of data values are shifted along the sensor array;*
   *f) reading the integrated data values from the sensor array to produce an image output representing a continuous view of the object;*
   *g) converting the image output into a video signal; and,*
   *h) determining at least one characteristic of the object from the video signal.*

*23. A method of quality control comprising the steps of:*
   *a) moving an object to be examined through an examination region along a path perpendicular to a field of view of a time delay and integration mode video camera;*
   *b) monitoring the movement of the object;*
   *c) illuminating the object as the object moves through the examination region;*
   *d) shifting lines of data values indicative of portions of the object along a sensor array of the time delay and integration mode video camera parallel to the object path in coordination with the monitored object movement;*
   *e) in real time, adjusting a rate of shifting the lines of data values along the sensor array in coordination with variations in the monitored movement of the object;*
   *f) integrating the data values indicative of the same portion of the object as the lines of data values are shifted along the sensor array;*
   *g) reading the integrated data values from the sensor array to produce an image output representing a continuous view of the object; and,*
   *h) determining at least one characteristic of the object from the image output.*

* * * * *